(12) United States Patent
Schoultz et al.

(10) Patent No.: US 9,949,879 B2
(45) Date of Patent: Apr. 24, 2018

(54) METHOD FOR ATTACHING DISCRETE WEB SEGMENTS

(71) Applicant: KIMBERLY-CLARK WORLDWIDE, INC., Neenah, WI (US)

(72) Inventors: Adam Schoultz, Neenah, WI (US); Brian Rhodes, Larsen, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 15/581,802

(22) Filed: Apr. 28, 2017

(65) Prior Publication Data

US 2017/0231829 A1  Aug. 17, 2017

Related U.S. Application Data

(62) Division of application No. 13/474,918, filed on May 18, 2012, now Pat. No. 9,668,923.

(51) Int. Cl.
| | | |
|---|---|---|
| *A61F 13/15* | (2006.01) | |
| *B32B 38/04* | (2006.01) | |
| *B65H 39/14* | (2006.01) | |

(52) U.S. Cl.
CPC .. *A61F 13/15747* (2013.01); *A61F 13/15577* (2013.01); *A61F 13/15756* (2013.01); *A61F 13/15764* (2013.01); *A61F 2013/15821* (2013.01)

(58) Field of Classification Search
CPC .......... A61F 13/15756; A61F 13/15764; A61F 13/15747; A61F 13/15577; B32B 38/0004; B32B 38/04; Y10T 156/1079; Y10T 156/12; Y10T 156/1317; Y10T 156/1322
See application file for complete search history.

(56) References Cited

U.S. PATENT DOCUMENTS

| | | | | |
|---|---|---|---|---|
| 3,770,540 A | * | 11/1973 | Fuchs ................. | B29C 66/0042 138/156 |
| 4,078,956 A | * | 3/1978 | Scheck ..................... | B26F 1/40 156/157 |
| 6,165,306 A | * | 12/2000 | Rajala ............... | A61F 13/15764 156/263 |
| 6,613,177 B1 | * | 9/2003 | Suda ................... | B29C 65/7891 156/264 |
| 8,002,924 B2 | * | 8/2011 | Machamer ......... | B65H 19/1836 156/157 |
| 2006/0263594 A1 | * | 11/2006 | Kraft ..................... | B31D 1/021 428/343 |

(Continued)

*Primary Examiner* — Mark A Osele
*Assistant Examiner* — Christopher C Caillouet
(74) *Attorney, Agent, or Firm* — Armstrong Teasdale LLP (57) ABSTRACT

A method of forming a web includes directing a first discrete segment at a first speed to a first pick-up location. The first discrete segment is transferred from the first pick-up location to an application location using a first segment transfer device. A second discrete segment is directed to at a second speed to a second pick-up location. The second discrete segment is transferred from the second pick-up location to the application location using a second segment transfer device. The first and second discrete segments are attached to each other at the application location to form a web.

20 Claims, 6 Drawing Sheets

(56) References Cited

U.S. PATENT DOCUMENTS

2007/0044898 A1* 3/2007 Hikita ............... B65H 19/1836
                                                          156/159
2011/0203431 A1* 8/2011 Cocozzella ............ A61F 13/15
                                                          83/23

* cited by examiner

METHOD FOR ATTACHING DISCRETE WEB SEGMENTS

CROSS-REFERENCE TO RELATED APPLICATION

This application is a divisional application of U.S. patent application Ser. No. 13/474,918 entitled APPARATUS FOR ATTACHING DISCRETE WEB SEGMENTS, filed May 18, 2012, the disclosure of which is fully incorporated herein by reference.

FIELD

The field of the invention relates generally to web handling apparatus and more specifically to web handling apparatus adapted to attach discrete web segments together to form a continuous web and a method of using the apparatus.

BACKGROUND

Some individuals rely on disposable absorbent products in their everyday lives including, for example, disposable absorbent articles such as adult incontinence products, enuresis pants, training pants, and diapers. Many manufacturers of these absorbent articles seek to better meet the needs of users. For example, there is an ongoing need to improve fit, discretion, and leakage protection for many of these articles.

Some absorbent articles employ elasticization across the front and/or back of the article to keep the article snug against the wearer during use. Some of these articles employ a multiplicity of elastic strands within front and/or back waist panels of the article to provide the elasticization, while others employ elastomeric polymeric films, which are often sandwiched with one or more nonwoven layers.

Most absorbent articles include an absorbent member, constructed from wood pulp fluff, superabsorbent polymers, and/or other absorbent material to absorb fluids (e.g., urine) discharged by the user. The absorbent member is typically positioned in the crotch region of the article and extends forward and backward into the article's front and/or back regions. In some absorbent articles, the elastic members that extend across the front and/or back waist panels of the article overlap the absorbent member at various locations since the absorbent member extends forward/backward into the front/back waist regions of the article.

Some absorbent articles include refastenable seams disposed along the sides of the article to enable the wearer or a caregiver to remove the article by detaching the front region from the back region along the seams. Because the refastenble seams are located along the sides of the article, some wearers find the seams difficult to manipulate. Refastenable side seams can also be difficult for some caregivers of bedridden individuals to manipulate.

Thus, there remains a need for apparatus and processes of manufacturing articles that have refastenable side seams that are easy to manipulate.

SUMMARY

In one aspect, apparatus for attaching discrete segments together to form a continuous web generally comprises a first segment transfer device adapted to receive a first continuous web at a first pick-up location and to release a first discrete segment cut from the first web at an application location. The first segment transfer device has a first speed profile. A second segment transfer device is adapted to receive a second continuous web at a second pick-up location and to release a second discrete segment cut from the second web at the application location such that the second discrete segment is attached to the first discrete segment. The second segment transfer device has a second speed profile that is different than the first speed profile.

In another aspect, apparatus for attaching discrete segments together to form a continuous web generally comprises a first segment transfer device sized and shaped to receive a first discrete segment having a first length at a first pick-up location and to release the first discrete segment at an application location. A second segment transfer device is sized and shaped to receive a second discrete segment having a second length at a second pick-up location and to release the second discrete segment at the application location such that the second discrete segment is attached to the first discrete segment. The first length of the first discrete segment is greater than the second length of the second discrete segment.

In yet another aspect, a method of forming a web generally comprises directing a first discrete segment at a first speed to a first pick-up location. The first discrete segment is transferred from the first pick-up location to an application location using a first segment transfer device. A second discrete segment is directed at a second speed to a second pick-up location. The second discrete segment is transferred from the second pick-up location to the application location using a second segment transfer device. The first and second discrete segments are attached to each other at the application location to form a web.

BRIEF DESCRIPTION OF THE DRAWINGS

Corresponding reference characters indicate corresponding parts throughout the drawings.

DETAILED DESCRIPTION OF THE DRAWINGS

Figure 1:
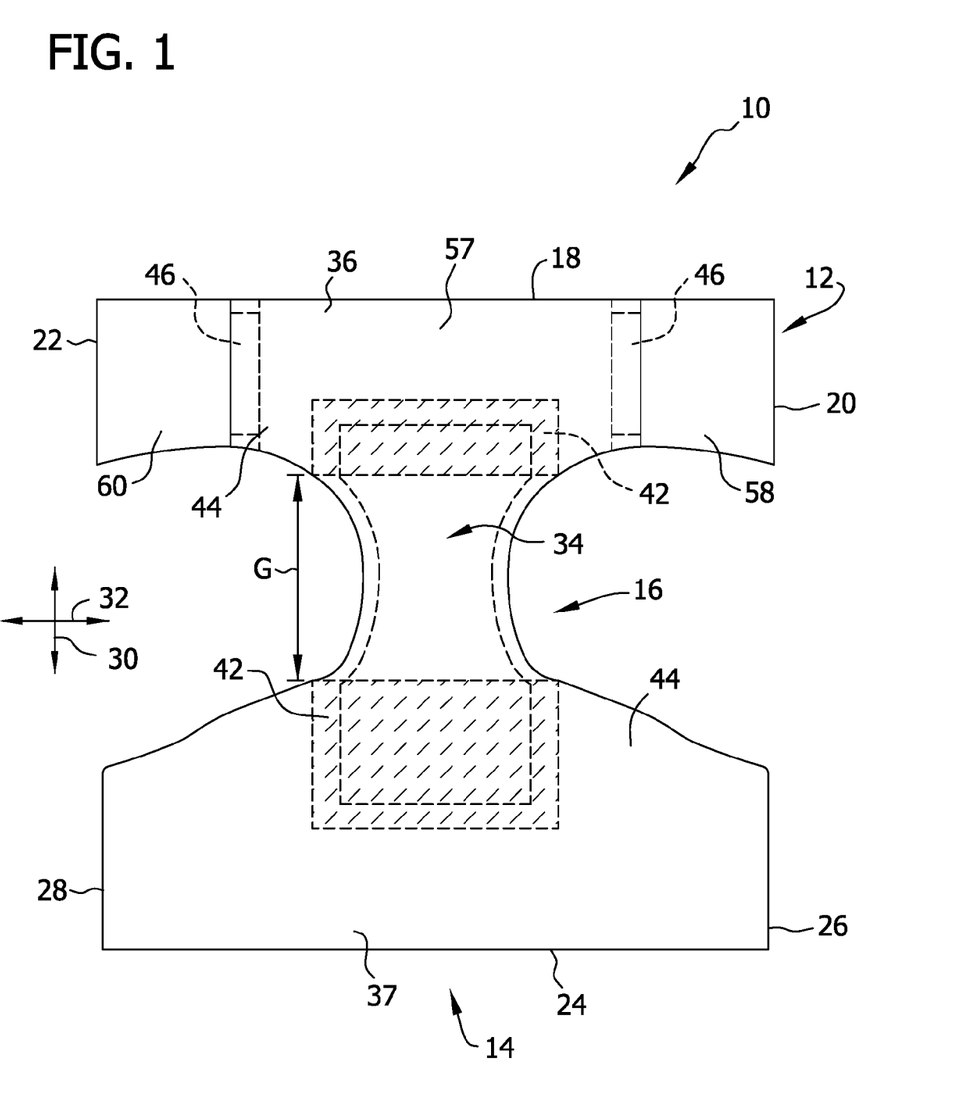
FIG. 1 is a plan view of one embodiment of an absorbent article, the article being in a longitudinally stretched and laid-flat condition showing a surface of the article that faces the wearer during wear.
Figure 2:
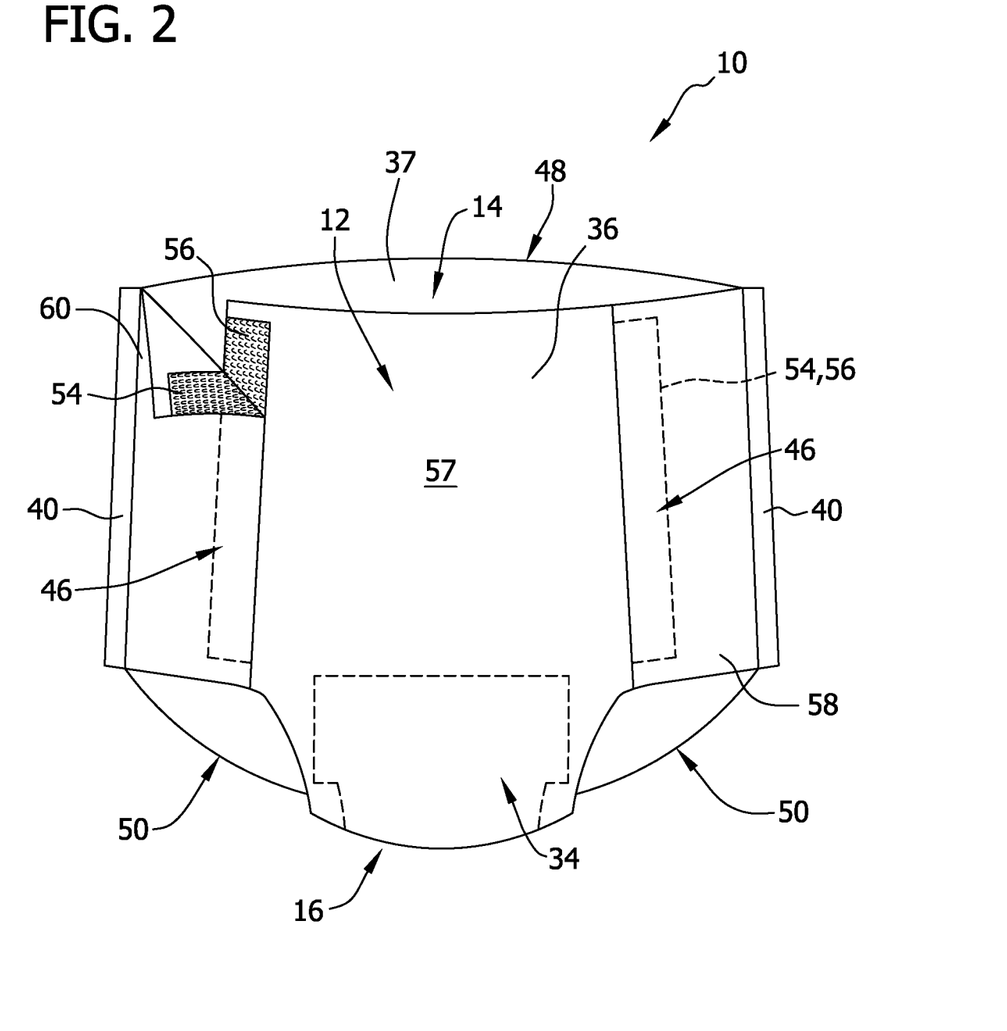
FIG. 2 is a front view of the absorbent article of FIG. 1 with front and back waist regions of the article joined by a fastening assembly such that the garment is in a pull-on, pant-like configuration.

FIGS. 1 and 2 illustrate one suitable embodiment of an absorbent article, indicated generally at 10. The absorbent article 10 has a front region 12, a back region 14, and a crotch region 16 disposed longitudinally between and interconnecting the front and back regions. The front, back and crotch regions 12, 14, 16 are indicated generally by the respective reference number. In the front region 12, the absorbent article 10 has a front edge 18 and transversely opposed first and second front side edges 20, 22. A back edge 24 and transversely opposed first and second back side edges 26, 28 are located in the back region 14 of the absorbent article 10. As illustrated in FIG. 1, the absorbent article 10 defines a longitudinal direction 30 and a transverse direction 32 perpendicular to the longitudinal direction.

The absorbent article 10 includes an absorbent insert, indicated generally at 34, that extends longitudinally from the front region 12 through the crotch region 16 to the back region 14. The absorbent insert 34 can be constructed of materials suitable for absorbing liquid excretions, such as wood pulp fluff, superabsorbent polymers, absorbent foam, and the like. The absorbent insert 34 can be encased in one or more substrates. For example, the absorbent insert 34 can be wrapped in a tissue and/or a nonwoven substrate.

In the illustrated embodiment, the front and back regions 12, 14 of the absorbent article 10 are constructed of separate pieces of laminate 36, 37 that are interconnected via the absorbent insert 34. That is, the front region 12 is formed by a piece of laminate 36 and the back region 14 is formed by a separate piece of laminate 37. As seen in FIG. 1, the laminate 36 forming the front region 12 is spaced from the laminate 37 forming the back region 14 to define a gap G. The absorbent insert 34 spans the gap G and connects the laminate 36 forming the front region 12 to the laminate 37 forming the back region 14.

As seen in FIG. 1, a portion of the absorbent insert 34 overlaps a portion of each of the laminates 36, 37 in the front and back regions 12, 14 to define overlapped regions 42 and non-overlapped regions 44. In one suitable embodiment, at least a portion of each of the overlapped regions 42 of the laminate 36 is non-elastomeric, and at least a portion of the non-overlapped region 44 of the laminate 36 is elastomeric. The overlapped regions 42 are indicated in FIG. 1 by a pattern of diagonally extending dashes.

In one suitable embodiment, each of the laminates 36, 37 forming the overlapped regions 42 in the front and back regions 12, 14 is constructed entirely of an elastomeric film laminate having portions thereof "deactivated" or "deadened" to render it non-elastomeric. As used herein, "elastomeric" refers to a material or composite that can be elongated by at least 50 percent of its relaxed length and that will recover, upon release of the applied force, at least 50 percent of its elongation. It is generally preferred that the elastomeric material or composite be capable of being elongated by at least 100 percent, more preferably by at least 200 percent, of its relaxed length and recover, upon release of an applied force, at least 50 percent of its elongation. "Non-elastomeric" refers to a material or composite that is non-extensible, or that is extensible but will recover no more than 20 percent of its elongated length after release of an applied elongating force. "Non-extensible" refers to a material that cannot stretch or extend by more than 25 percent of its relaxed length without fracture upon application of a biasing force. "Partially elastomeric" refers to a material or composite which can be elongated by at least 50 percent of its relaxed length and which will recover, upon release of the applied force, more than 20 percent but less than 50 percent of its elongation.

It should be noted that in analyzing the laminates 36, 37 or regions thereof for extensible or elastic character, the laminates are to be examined with any separately attached components removed. For example, before examining the extensible or elastic properties of the overlapped regions 42 of the laminates 36, 37, the absorbent insert 34 should be removed. That is, the absorbent insert 34 should be peeled away from the laminates 36, 37 prior to examining the extensibility or elasticity of any portion of the laminates.

In one suitable embodiment, the majority of the overlapped region 42 of each of the laminates 36, 37 is non-elastomeric. That is, more than 50 percent of the area of the overlapped region 42 of the laminates 36, 37 is non-elastomeric. In one suitable embodiment, more than 75 percent, and in still a more suitable embodiment, more than 90 percent of the area of the overlapped region 42 of the laminates 36 is non-elastomeric. In another suitable embodiment, the entire overlapped region 42 of the laminates 36, 37 (i.e., 100 percent) is non-elastomeric. For example, in the absorbent article 10 illustrated in FIG. 1, the entire overlapped region 42 of the laminates 36, 37 is non-elastomeric and generally the same size and shape as the portion of the absorbent insert 34 that overlaps it.

In other suitable embodiments, the portion of the laminates 36, 37 rendered non-elastomeric can be larger than the corresponding overlapped region 42. For example, the non-elastomeric area of the laminates 36, 37 can be 125 percent or less larger, more preferably 120 percent or less larger, and still more preferably 110 percent or less larger in area than the overlapped region 42. By having the non-elastomeric region of the laminates 36, 37 larger than the area of the overlapped regions 42, it is possible to accommodate the process registration variability common in typical high-speed absorbent article manufacturing processes. In other words, the footprint of the non-elastomeric region of the laminates 36, 37 being larger relative to the footprint of the absorbent insert 34 in the front and back regions 12, 14 of the absorbent article 10 allows for variability in registration as the absorbent insert is mated to the laminates. Furthermore, in such embodiments, the relatively larger non-elastomeric region (larger relative to the overlapped region 42) will aid in minimizing the amount of bunching directly around the periphery of the absorbent insert 34, which can provide a smoother, "flatter", more underwear-like garment.

In the illustrated embodiment, the laminate 36 used to form the front region 12 of the absorbent article 10 comprises a center panel 57 and a pair of side panels 58, 60. As seen in FIG. 1, one of the panels 58 extends outward from one side (i.e., the right side as viewed in FIG. 1) of the center panel 57 and the other panel 60 extends outward from the other side (i.e., the left side as viewed in FIG. 1) of the center panel. Suitably, the side panels 58, 60 have properties or characteristics that are different than properties or characteristics of the center panel 57. In one suitable example, each of the side panels 58, 60 are more elastic or stretchable than the center panel. It is understood that the side panels 58, 60 can have other properties (e.g., strength) in addition to or instead of elasticity or stretchability that differ from the center panel.

In one suitable embodiment, the center panel 57 of the front region 12 comprises a polymeric film layer and at least one nonwoven layer. In the illustrated embodiment, for example, the center panel 57 comprises two nonwoven layers superposed on opposing top and bottom surfaces of the polymeric film layer such that the polymeric film layer is sandwiched between the two nonwoven layers. The polymeric film layer and both nonwoven layers extend substantially throughout the entire area of the center panel.

The illustrated side panels 58, 60 of the front region also comprise a polymeric film layer and at least one nonwoven layer. More specific, each of the side panels 58, 60 comprises two nonwoven layers superposed on opposing top and bottom surfaces of the polymeric film layer such that the polymeric film layer is sandwiched between the two nonwoven layers. As mentioned above, in one suitable embodiment the material(s) used to form the side panels 58, 60 are more elastic or stretchable than the material(s) used to form the center panel 57. It is understood, however, that the material(s) used to form the side panels 58, 60 can have other properties (e.g., strength) in addition to or instead of elasticity or stretchability that differ from the material(s) used to form the center panel 57.

In one suitable embodiment, the laminate 37 used to form the back region 14 of the absorbent article 10 comprises a polymeric film layer and at least one nonwoven layer. In the illustrated embodiment, for example, the laminate 37 has two nonwoven layers superposed on opposing top and bottom surfaces of the polymeric film layer such that the polymeric film layer is sandwiched between the two nonwoven layers. The polymeric film layer and both nonwoven layers extend substantially throughout the entire area of the laminate 37. While the laminate 37 used to form the back region 14 is the same throughout the back region in the illustrated absorbent article 10, it is contemplated that different laminates or materials can be used in different parts of the back region.

In the illustrated embodiment, the material(s) used to form the center panel 57 of the front region 12 and the laminate 37 of the back region 14 are substantially the same. It is understood, however, that the material(s) used to form the center panel 57 of the front region 12 can be different than those used to form the laminate 37 of the back region 14 of the absorbent article 10.

Figure 3:
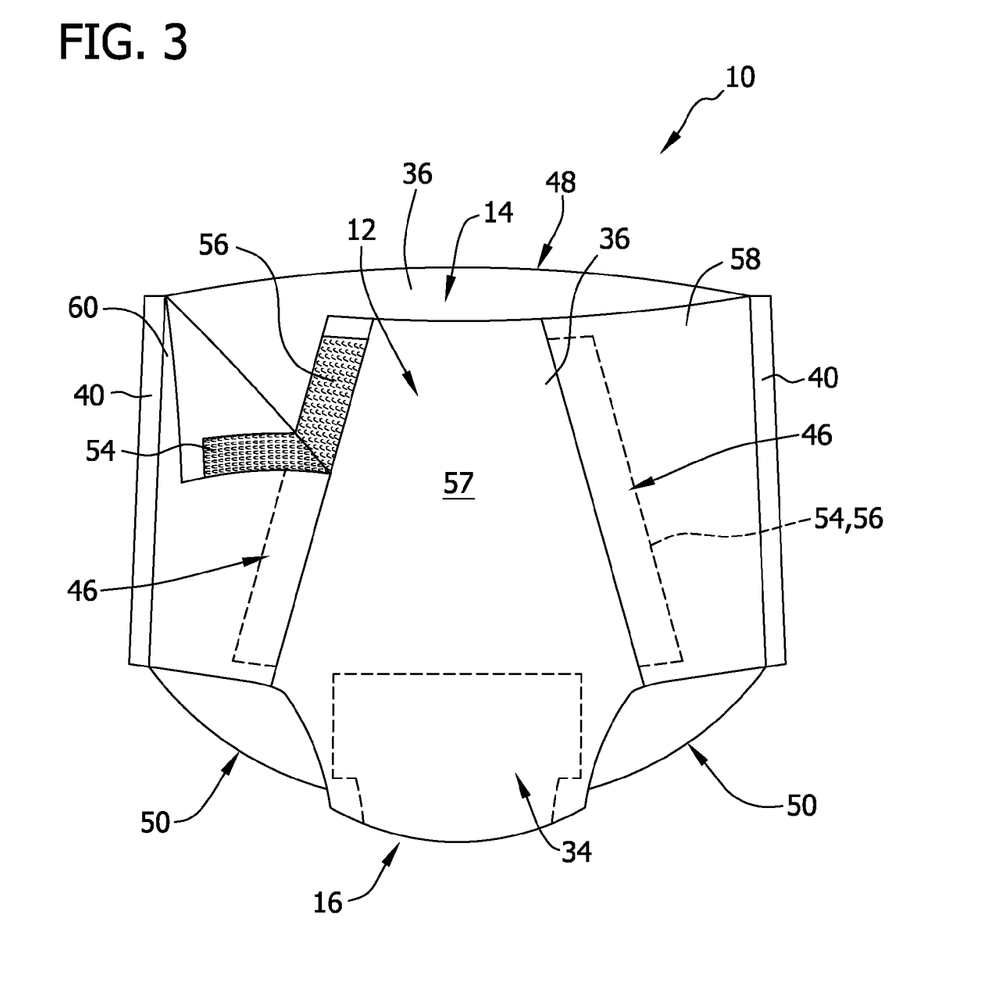
FIG. 3 is another front view of the absorbent article of FIG. 1 with another embodiment of a fastening assembly.

As seen in FIGS. 2 and 3, the front region 12 of the absorbent article 10 is joined to the back region 14 via a pair of non-refastenable butt seams 40 to define a pull-on, pant-like configuration of the absorbent article having a waist opening, indicated at 48, and two leg openings, indicated at 50. More specifically, a portion of the front region 12 adjacent the first and second front side edges 20, 22 of the front region 12 are joined to a portion of the back region 14 adjacent the first and second back side edges 26, 28 of the back region 14. While FIGS. 2 and 3 illustrate the front and back regions 12, 14 being joined together via butt seams 40, it is understood that the front and back regions can be joined together via other types of non-refastenable seams (e.g., overlapping seams).

With reference still to FIGS. 2 and 3, the absorbent article 10 includes at least one fastening assembly, indicated generally at 46, disposed in the front region 12 of the absorbent article. In the illustrated embodiment, the fastening assembly 46 includes a left-handed fastening assembly member attached to one of the side panels 58 of the front region 12, and a right-handed fastening assembly attached to the other side panel 60 of the front region 12. Each of the fastening assemblies 46 includes a pair of fastener members 54, 56 that are attached to the front region 12 in spaced relationship with the butt seams 40. Thus, each of the fastener members 54, 56 is spaced from the back region 14 of the absorbent article 10.

As a result, the absorbent article 10 can be selectively moved between an opened configuration wherein at least one of the fastening assemblies 46 are disengaged (i.e., where the fastener members 54, 56 not attached), and a closed configuration wherein both of the fastening assemblies are engaged (i.e., wherein the fastener members 54, 56 attached). As illustrated in FIG. 3, the fastening assemblies 46 can be angled relative to the longitudinal direction 30 of the absorbent article 10.

In the illustrated embodiment, the fastener members 54 on the side panels 58, 60 comprise hook fasteners and the other fastener members 56 comprise complementary loop fasteners. In another suitable embodiment, the fastener members 54 on the side panels 58, 60 can comprise loop fasteners and the other fastener members 56 can comprise complementary hook fasteners. It is contemplated that the loop fasteners can be formed integral with either the side panels 58, 60 or the center panel 57 such that the complementary hook fastener can be engaged anywhere on the respective side panel or center panel. In other suitable embodiments, the fastener members 54, 56 can comprise other suitable fasteners, adhesive or cohesive fastening elements such as an adhesive fastener and an adhesive-receptive landing zone or material, or the like.

Figure 4:
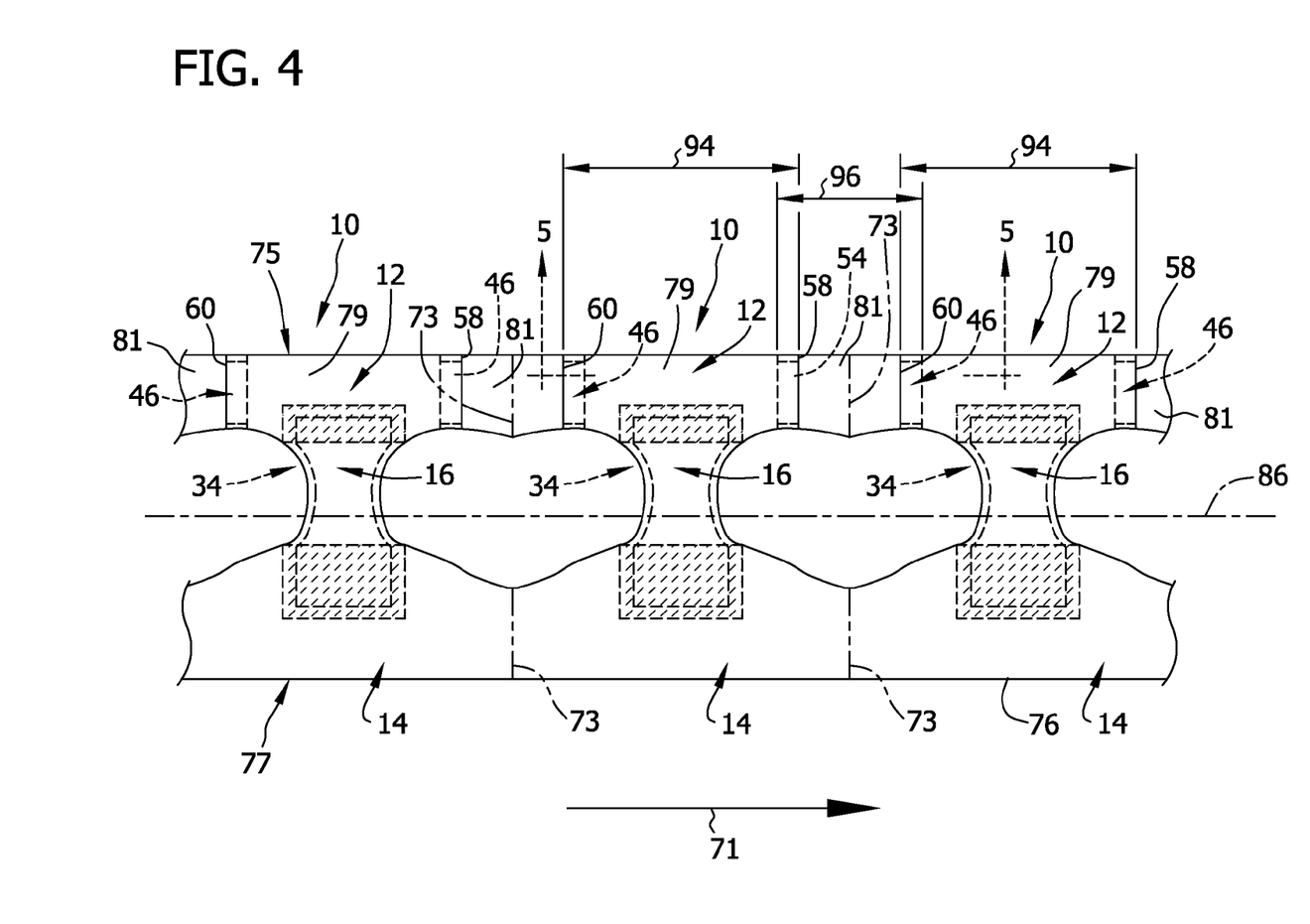
FIG. 4 illustrates a portion of a manufacturing process for manufacturing the absorbent article illustrated in FIGS. 1-3.

FIG. 4 illustrates a plurality of absorbent articles 10 (e.g., three absorbent articles being illustrated in FIG. 4) in the process of being manufactured. More specifically, FIG. 4 illustrates the plurality of absorbent articles 10 moving in a cross-machine direction (indicated by arrow 71) and prior to being cut into discrete articles 10 along cut lines 73. As seen in FIG. 4, each of the front regions 12 of the illustrated articles 10 are formed from a continuous web 75 and each of the back regions 14 of are formed from a separate continuous web 77. The absorbent inserts 34, which are discrete pieces, have been bonded in spaced relationship with each other along the length of the continuous webs 75, 77.

In the illustrated embodiment, the continuous web 77 forming the back regions 14 of the absorbent articles 10 is formed from a single material (e.g., laminate 37). The continuous web 75 forming the front regions 12 of the illustrated articles 10, however, is formed from discrete segments of at least two different materials. More specifically, the continuous web 75 forming the front regions 12 of the articles 10 comprises a plurality of first discrete segments 79 and a plurality of second discrete segments 81. As seen in FIG. 4, the first and second discrete segments 79, 81 overlap each other and are connected to each other within the overlap.

Figure 5:
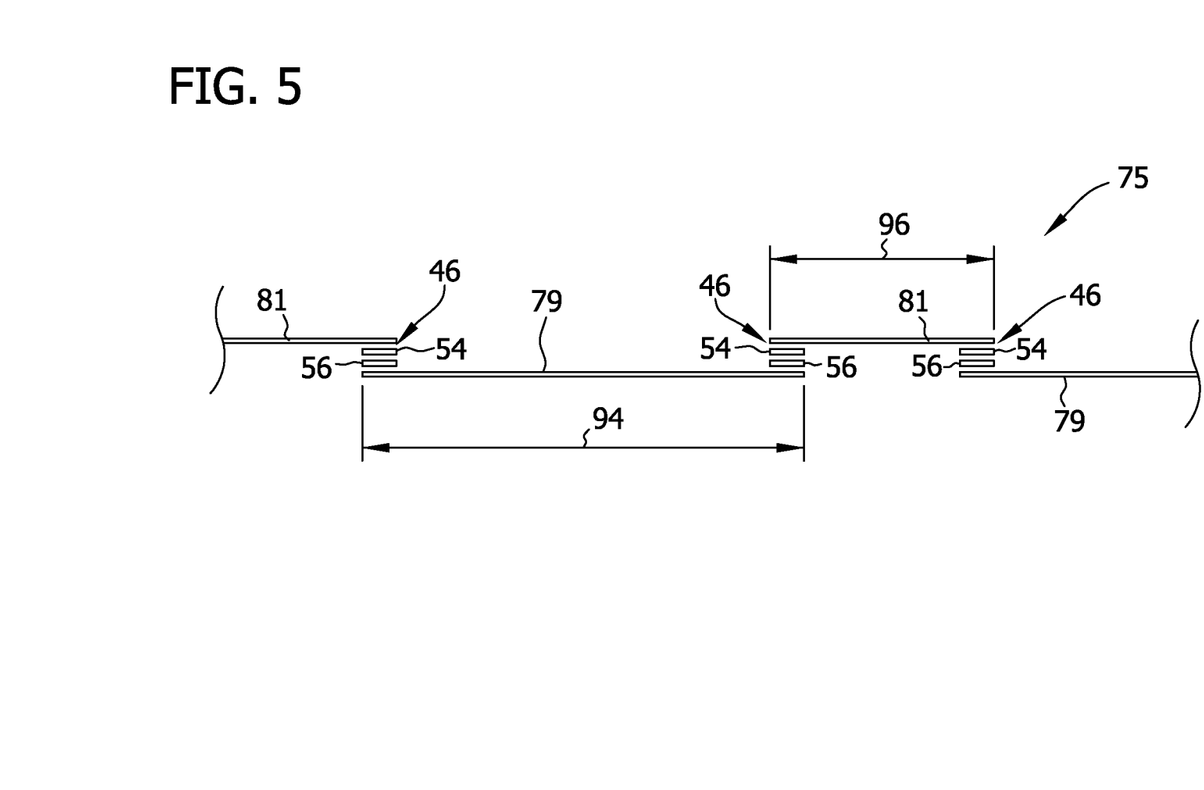
FIG. 5 is cross-section taken along 5-5 of FIG. 4.

As seen in FIGS. 4 and 5, the first discrete segments 79 has a first length 94 and the second discrete segments 81 a second length 96 that is less than the first length. As seen in FIGS. 4 and 5, each of the first discrete segments 79 defines the center panel 57 of one of the absorbent articles 10 and each of the second discrete segments 81 defines one of the side panels 60 of a leading absorbent article and one of the side panels 58 of a trailing absorbent article. That is, each of the second discrete segments defines two side panels 58, 60, with each of the side panels being located on different (adjacent) absorbent articles 10.

It is contemplated that back region 14 of the articles 10 can be formed from discrete segments instead of or in addition to the front region 12 of the article being formed from discrete segments. It is also contemplated that the first and second discrete segments 79, 81 can have substantially the same length or that the first length 94 of the first discrete segment can be less than the second length 96 of the second discrete segment. It is further contemplated that the first and second discrete segments 79, 81 can be formed from the same material instead of different materials as illustrated in FIGS. 4 and 5.

Figure 6:
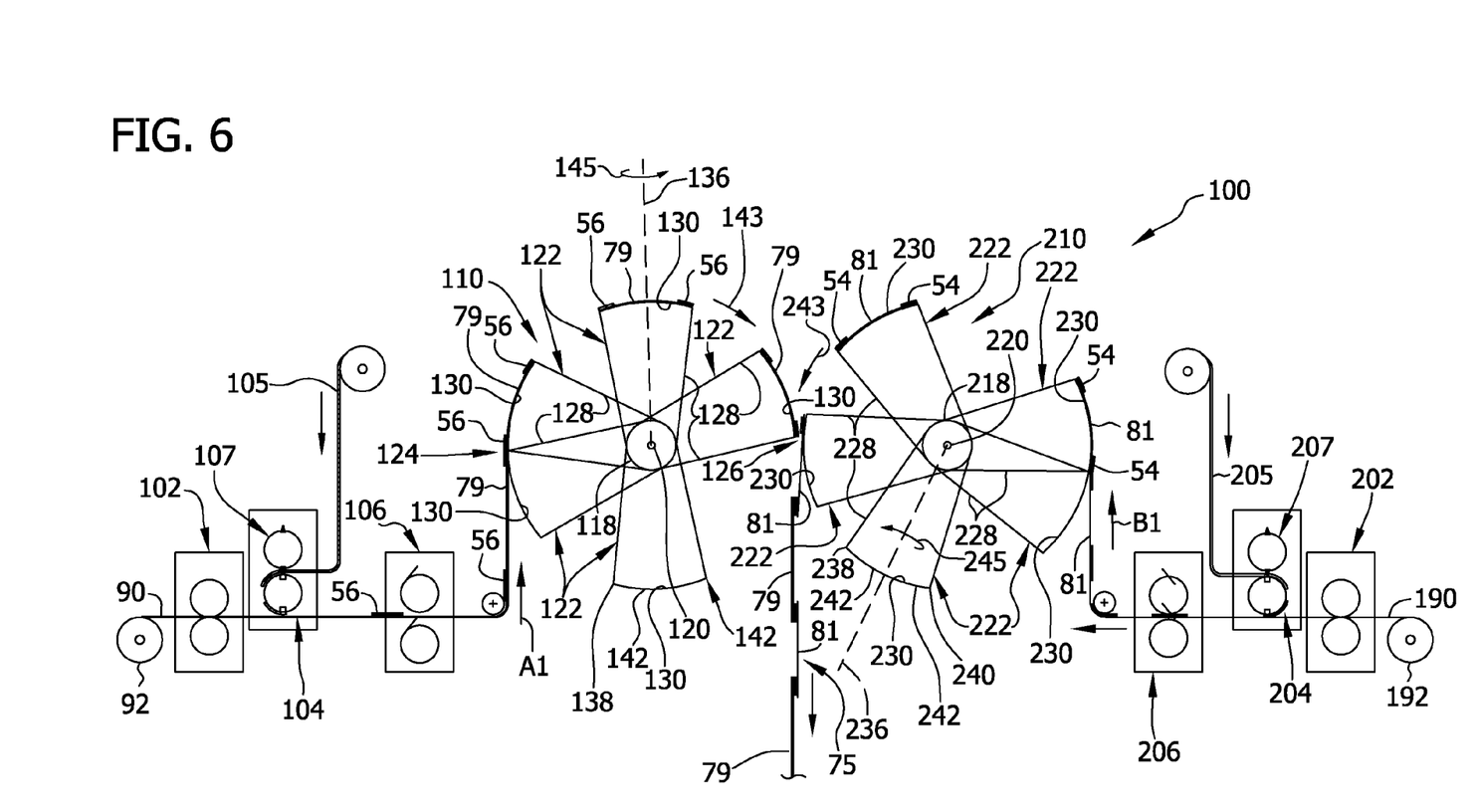
FIG. 6 illustrate a portion of one embodiment of a manufacturing process for manufacturing a web suitable for use in the manufacturing the absorbent article.

FIG. 6 schematically illustrates a portion of one suitable embodiment of an apparatus, indicated generally at 100, for making the continuous web 75 illustrated in FIGS. 4 and 5 and used to form the front region 12 of the illustrated absorbent article 10. As seen in FIG. 6, a supply of web 90 (e.g., a web of material suitable for the center part 57 of the front region 12 of the absorbent article 10) used to form the first discrete segment 79 of the absorbent article 10 is provided from a suitable supply source (e.g., supply roll 92). In the illustrated embodiment, the web 90 is fed from the supply roll 92 by a web transfer device, indicated generally at 102, to a bonding station, indicated generally at 104.

One of the fastener member (e.g., in the illustrated embodiment, loop fastener member 56) are bonded to the web 90 at the bonding station 104. In the illustrated embodiment, the loop fastener members 56 are bonded (e.g., thermally bonded, point bonded, adhesively bonded) to the continuous web 90. As seen in FIG. 6, the loop fastener members 56 are fed to the bonding station 104 from a continuous supply web 105 after they have been cut into suitably sized segments by a cutting device, indicated generally at 107 (e.g., a knife and anvil roll as seen in FIG. 6). It is contemplated that the web 90 can be made from materials suitable for use as the loop fastener members 56. In such an embodiment, the supply web 105, the cutting device 107 and bonding station 104 can be eliminated.

The web 90 having loop fastener members 56 bonded thereto is then fed to a suitable cutting device, indicated at 106. In the illustrated embodiment, the cutting device 106 is arranged to perforate each of the loop fastener members 56 and the portion of the web 90 underlying the loop fastener members 56 to define a line of weakness extending in a cross-machine direction of the web. It is contemplated that the cutting device 106 can be arranged to cut (i.e., sever) or otherwise form lines of weakness on the loop fastener members 56 and the underlying web portion.

As seen in FIG. 6, the web 90 is then fed to a first segment transfer device, indicated generally at 110. More specifically, the first segment transfer device 110 receives the web 90 as it is traveling in a first direction, represented by arrow A1. In the illustrated embodiment, the web 90 includes a plurality of first segments separated by the lines of weakness (i.e., perforations) formed in the web by the cutting device 106. It is contemplated, however, that the plurality of first segments can be fed to the first segment transfer device 110 as separate segments. That is, a plurality of first discrete segments 79 can be individually fed to the first segment transfer device 110. It is also contemplated that the web 90 can be cut into a plurality of first discrete segments 79 while the web is disposed on the first segment transfer device 110.

In one suitable embodiment, the first segment transfer device 110 includes a drive assembly 118 configured to rotate about a drive axis 120, and a plurality of transfer elements 122 coupled to and extend outward from the drive assembly. The drive assembly 118 includes one or more suitable drive sources including, for example, servo motors, and/or camboxes, operatively connected to each of the transfer elements 122. More specifically, the drive source(s) of the drive assembly 118 is configured to rotate each transfer element 122 about the drive axis 120 between a pick-up location, indicated generally at 124, and an application (or drop-off) location, indicated generally at 126. In the illustrated embodiment, the drive assembly 118 is configured to rotate each of the transfer elements 122 in a clockwise direction (as viewed in FIG. 6).

As illustrated in FIG. 6, each of the transfer elements 122 is configured to receive the web 90 at the pick-up location 124, and convey each of the first discrete segments 79 to the application location 126. In the illustrated configuration, each of the first discrete segments 79 is separated from an adjacent first discrete segment along the preformed perforation (or other line of weakness) as the web 90 is initially conveyed by the first segment transfer device 110. More specifically, each of the first discrete segments 79 is received by one of the transfer elements 122 while it is still connected to the web 90.

As illustrated in FIG. 6, two of the transfer elements 122 are disposed in close proximity to each other as the web 90 is initially received by the first segment transfer device 110. As a result, the web 90 can be continuous fed to the first segment transfer device 110 with each of the first discrete segments 79 being received by one of the transfer elements 122.

During each full rotation of the first segment transfer device 110, each of the transfer elements 122 rotates along a first variable speed profile. In other words, the transfer elements 122 of the first segment transfer device 110 rotate at variable speeds during each revolution. For example, each of the transfer elements 122 rotates at a first transfer speed (as measured at the outer surface of the transfer element 122). Preferably, the first transfer speed of the transfer elements 122 approximately matches the speed at which the web 90 of first discrete segments 79 is being fed to the first segment transfer device 110.

After one of the first discrete segments 79 is received by one of the transfer elements 122, the drive assembly 118 accelerates the transfer element to a second, faster transfer speed. As a result, the accelerated transfer element 122 separates from the adjacent, trailing transfer element. Thus, the two transfer elements 122 that were adjacent at the pick-up location 124 are moved apart which causes the web 90 of first discrete segments 79 to rupture about the preformed perforations and thereby separate the first discrete segment from the web.

As seen in FIG. 6 and described in more detail below, each of the first discrete segments 79 is attached to one of the second discrete segments 81 at the application location 126 to form the continuous web 75. After the first discrete segment 79 traveling on the transfer element 122 is attached to second discrete segments 81, the first discrete segment is released from the transfer element.

Each of the transfer elements 122 decelerate from the second transfer speed back to the slower, first transfer speed as it approaches the pick-up location 124. Accordingly, in the illustrated embodiment, the first variable speed profile of the first segment transfer device 110 comprises accelerating each of the transfer elements 122 from the first transfer speed at the pick-up location 124 to the second, faster transfer speed at the application location 126 and then decelerating each of the transfer elements from the second transfer speed to the first transfer speed as the transfer element rotates from the application location back to the pick-up location. It is understood, however, that the first segment transfer device 110 can have a different speed profile without departing from some aspects of this invention.

In one suitable embodiment, the first segment transfer device 110 is an oscillating cam adjusted roller as is disclosed in U.S. Pat. Nos. 5,716,478, 5,759,340, and 6,139,004, all of which are assigned to Kimberly-Clark Worldwide, Inc., and the entire disclosures of all of which are hereby incorporated herein by reference. It is understood, however, that the first segment transfer device 110 can comprise other types of suitable web accelerators. For example, in another suitable embodiment, the first segment transfer device 110 can comprise known slip-cut apparatus.

With reference still to FIG. 6, each of the transfer elements 122 includes a support arm 128 extending radially outwardly from the drive assembly 118, and a transfer puck 130 rotatably coupled to the support arm 128. The support arm 128 includes a first end, which is coupled to the drive assembly 118, and an opposite second end, which is coupled to the transfer puck 130. The support arm 128 extends between the first end and the second end along a radial axis 136 of the transfer element 122. In one suitable embodiment, the first end of the support arm 128 is coupled to the drive assembly 118 such that each transfer puck 130 is independently rotatable about both the drive axis 120 of the first segment transfer device 110 (as indicated by arrow 143 of FIG. 6) and the radial axis (as indicated by arrow 145 of FIG. 6). It is understood, however, that each of the transfer elements 122 can be fixed to inhibit rotation of the corresponding transfer puck 130 about the radial axis 136.

As illustrated in FIG. 6, each transfer puck 130 includes a leading edge 138, a trailing edge 140, and a platform 142 that extends between the leading edge and the trailing edge. The platform 142 of each of the transfer pucks 130 is sized and shaped to receive and hold one of the first discrete segments 79. The first discrete segments 79 can be held to the transfer puck 130 by vacuum, surface roughness and/or needle engagement. It is also contemplated that the transfer puck 130 can include a raised pad (e.g., a polymer insert) for receiving each of the loop fastener members 56. The raised pad can be used to increase the engagement pressure (i.e., compression) between the fastener members 54, 56 at the application location 126.

As mentioned above, the transfer puck 130 is pivotable about the support arm axis 136. Thus, the orientation of each of the transfer pucks 130 can be adjusted or altered. As a result, the orientation of the first discrete segments 79 can be adjusted or altered as it is received by the first segment transfer device 110. For example, each of the first discrete segments 79 can be received on the transfer pucks 130 in a first orientation (e.g., a machine direction), such as at the pick-up location 124 and rotated to a second orientation (e.g., a cross-machine direction) prior to the application location 126. That is, each of the first discrete segments 79 can be fed to the first segment transfer device 110 in the machine direction (or the cross-machine direction) at the pick-up location 124 and rotated such that each of the first discrete segments 79 is in the cross-machine direction (or the machine direction) at the application location 126.

As also seen in FIG. 6, a supply of second web 190 (e.g., a web of material suitable for the side panels 58, 60 of the front region 12 of the absorbent article 10) used to form the second discrete segment 81 of the absorbent article 10 is provided from a suitable supply source (e.g., supply roll 192). In the illustrated embodiment, the web 190 is fed from the supply roll 192 by a web transfer device, indicated generally at 202, to a bonding station, indicated generally at 204.

One of the fastener members (e.g., in the illustrated embodiment, hook fastener member 54) is bonded to the web 190 at the bonding station 204. In the illustrated embodiment, the hook fastener members 54 are bonded (e.g., thermally bonded, point bonded, adhesively bonded) to the continuous web 190. As seen in FIG. 6, the hook fastener members 54 are fed to the bonding station 204 from a continuous supply web 205 after they have been cut into suitably sized segments by a suitable cutting device, indicated generally at 207 (e.g., a knife and anvil roll as seen in FIG. 6).

The web 190 having hook fastener members 54 bonded thereto is fed to a suitable cutting device, indicated at 206. In the illustrated embodiment, the cutting device 206 is arranged to perforate each of the hook fastener members 54 and the portion of the web 190 underlying the hook fastener members to define a line of weakness extending in a cross-machine direction of the web. It is contemplated that cutting device 206 can be arranged to cut (or sever) or otherwise form lines of weakness on the hook fastener members 54 and the underlying web portion.

As seen in FIG. 6, the web 190 is fed to a second segment transfer device, indicated generally at 210. More specifically, the second segment transfer device 210 receives the web 190 as it is traveling in a first direction, represented by arrow B1. In the illustrated embodiment, the web 190 includes a plurality of second discrete segments 81 separated by the lines of weakness (i.e., perforations) formed in the web by the cutting device 206. It is contemplated, however, that the plurality of second discrete segments 81 can be fed to the second segment transfer device 210 as separate segments. That is, a plurality of second discrete segments 81 can be individually fed to the second segment transfer device 210. It is also contemplated that the web 190 can be cut into a plurality of second discrete segments 81 while the web is disposed on the second segment transfer device 210.

In one suitable embodiment, the second segment transfer device 210 includes a drive assembly 218 configured to rotate about a drive axis 220, and a plurality of transfer elements 222 coupled to and extend outward from the drive assembly. The drive assembly 218 includes one or more suitable drive sources including, for example, servo motors, and/or camboxes, operatively connected to each of the transfer elements 222. More specifically, the drive source(s) of the drive assembly 218 is configured to rotate each transfer element 222 about the drive axis 220 between a pick-up location, indicated generally at 224, and the application location 126. In the illustrated embodiment, the drive assembly 218 is configured to rotate each of the transfer elements 222 in a counterclockwise direction (as viewed in FIG. 6).

As illustrated in FIG. 6, each of the transfer elements 222 is configured to receive the web 190 at the pick-up location 224, and convey each of the second discrete segments 81 to the application location 126. In the illustrated configuration, each of the second segments is separated from an adjacent segment along the preformed perforation (or other line of weakness) as the web 190 is initially conveyed by the second segment transfer device 210. More specifically, each of the second segments is received by one of the transfer elements 222 while it is still connected to the web 190.

As illustrated in FIG. 6, two of the transfer elements 222 are disposed in close proximity to each other as the web 190 is initially received by the second segment transfer device 210. As a result, the web 190 can be continuous fed to the second segment transfer device 210 with each of the second discrete segments 81 being received by one of the transfer elements 222.

During each full rotation of the second segment transfer device 210, each of the transfer elements 222 rotate along a second variable speed profile. In other words, the transfer elements 222 of the second segment transfer device 210 rotate at variable speeds during each revolution. For example, each of the transfer elements 222 rotates at a first transfer speed (as measured at the outer surface of the transfer element 222). Preferably, the first transfer speed of the transfer elements 222 approximately matches the speed at which the web 190 of second discrete segments 81 is being fed to the second segment transfer device 210.

After one of the second discrete segments 81 is received by one of the transfer elements 222, the drive assembly 218 accelerates the transfer element to a second, faster transfer speed. As a result, the accelerated transfer element 222 separates from the adjacent, trailing transfer element. Thus, the two transfer elements 222 that were adjacent at the pick-up location 224 are moved apart which causes the web 190 of second discrete segments 81 to rupture about the preformed perforations and thereby separate the second discrete segment from the web.

As seen in FIG. 6, each of the second discrete segments 81 is attached to one of the first discrete segments 79 at the application location 126 to form the continuous web 75. More specifically, in the illustrated embodiment, the leading loop fastener member 54 bonded to the second discrete segment 81 carried by one of the transfer element 222 of the second segment transfer device 210 is pressed into engagement with a trailing hook fastener member 56 bonded to one of first discrete segments 79 carried by one of the transfer elements 122 of the first segment transfer device 110 at the application location 126. The trailing loop fastener member 54 of the same second discrete segment 81 is then pressed into engagement with a leading hook fastener member 56 bonded to a different, trialing first discrete segment 79 (i.e., the first discrete segment 79 being carried by the following transfer element 122) at the application location 126. This process is continued to form continuous web 75.

Thus, the continuous web 75 is defined by a plurality of alternating first and second discrete segments 79, 81 with the first and second discrete segments being secured to each other by hook and loop fastener members 54, 76. It is contemplated that the alternating first and second discrete segments 79, 81 can be releasably secured to each other in other suitable ways or can be non-releasably secured (i.e., bonded) to each other without departing from some aspects of this invention. For example, the first and second discrete segments 79, 81 can be non-releasable secured together at the application location 126 by adhesive bonding, ultrasonic bonding, cohesive bonding, pressure bonding, and/or thermal bonding.

After the second discrete segment 81 traveling on the transfer element 222 is attached between a pair first discrete segments 79, the second discrete segment is released from the transfer element. As illustrated in FIG. 6, each of the transfer elements 222 decelerate from the second speed back to the slower, first speed as it approaches the pick-up location 224.

Accordingly, in the illustrated embodiment, the second variable speed profile of the second segment transfer device 210 comprises accelerating each of the transfer elements 222 from the first transfer speed at the pick-up location 224 to the second, faster transfer speed at the application location 126 and then decelerating each of the transfer elements from the second transfer speed to the first transfer speed as the transfer element rotates from the application location back to the pick-up location. It is understood, however, that the second segment transfer device 210 can have a different speed profile without departing from some aspects of this invention. It is also understood that in one embodiment, the first and second segment transfer devices 110, 210 can have substantially the same speed profile.

In one suitable embodiment, the second segment transfer device 210 is an oscillating cam adjusted roller as is disclosed in U.S. Pat. Nos. 5,716,478, 5,759,340, and 6,139,004, all of which are assigned to Kimberly-Clark Worldwide, Inc., and the entire disclosures of all of which are hereby incorporated herein by reference. It is understood, however, that the second segment transfer device 210 can comprise other types of suitable web accelerators. For example, in another suitable embodiment, the second segment transfer device 210 can comprise known slip-cut apparatus.

In the illustrated embodiment, the first and second segment transfer devices 110, 210 are both oscillating cam adjusted rollers. But it is understood that the first and second segments transfer device 110, 210 can differ. For example, the first segment transfer device 110 can comprise an oscillating cam adjusted roller and the second segment transfer device 210 can comprise a suitable slip-cut apparatus or vice versa. It is further understood that the first and second segment transfer devices 110, 210 can be any suitable web accelerators.

With reference still to FIG. 6, each of the transfer elements 222 includes a support arm 228 extending radially outwardly from the drive assembly 218, and a transfer puck 230 rotatably coupled to the support arm 228. The support arm 228 includes a first end, which is coupled to the drive assembly 218, and an opposite second end, which is coupled to the transfer puck 230. The support arm 228 extends between the first end and the second end along a radial axis 236 of the transfer element 222. In one suitable embodiment, the first end of the support arm 228 is coupled to the drive assembly 218 such that each transfer puck 230 is independently rotatable about both the drive axis 220 of the second segment transfer device 210 (as indicated by arrow 243 of FIG. 6) and the radial axis (as indicated by arrow 245 of FIG. 6). It is understood, however, that each of the transfer elements 222 can be fixed to inhibit rotation of the corresponding transfer puck 230 about the radial axis 236.

As illustrated in FIG. 6, each transfer puck 230 includes a leading edge 238, a trailing edge 240, and a platform 242 that extends between the leading edge and the trailing edge. The platform 242 of each of the transfer pucks 230 is sized and shaped to receive and hold one of the second discrete segments 81. The second discrete segments 81 can be held to the puck 230 by vacuum, surface roughness and/or needle engagement. It is also contemplated that the transfer puck 230 can include a raised pad (e.g., a polymer insert) for receiving each of the fastener members 54. The raised pad can be used to increase the engagement pressure (i.e., compression) between the fastener members 54, 56 at the application location 126.

As mentioned above, the transfer puck 230 is pivotable about the support arm axis 236. Thus, the orientation of each of the transfer pucks 230 can be adjusted or altered. As a result, the orientation of the second discrete segments 81 can be adjusted or altered. For example, each of the second discrete segments 81 can be received on the transfer pucks 230 in a first orientation (e.g., a machine direction), such as at the pick-up location 224 and rotated to a second orientation (e.g., a cross-machine direction) prior to the application location 126. That is, the second discrete segments 81 can be fed to the second segment transfer device 210 in the machine direction (or the cross-machine direction) at the pick-up location 124 and rotated such that the second discrete segments 81 are in the cross-machine direction (or the machine direction) at the application location 126.

In one suitable embodiment, the apparatus 100 includes an inspection system configured to ensure that each of the transfer elements 122, 222 of the first and second segment transfer devices 110, 220 are indeed transferring one of the first or second discrete segments 79, 81 and/or that the first or second discrete segments being transferred by the transfer elements are properly aligned. The inspection system can be integrated with a control system for the apparatus 100 such that the first and second segment transfer devices 110, 220 can be adjusted (i.e., sped up, slowed down, stopped) to accommodate for the situation wherein one or more of the first or second discrete segments 79, 81 are missing or misaligned on one or more of the transfer elements 122, 222. Misaligned first or second discrete segments 79, 81 can be aligned or culled.

When introducing elements of the present invention or the preferred embodiment(s) thereof, the articles "a", "an", "the", and "said" are intended to mean that there are one or more of the elements. The terms "comprising," "including", and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A method of forming a web comprising:
   directing a first discrete segment at a first speed to a first pick-up location;
   transferring the first discrete segment from the first pick-up location to an application location using a first segment transfer device;
   directing a second discrete segment at a second speed to a second pick-up location;
   transferring the second discrete segment from the second pick-up location to the application location using a second segment transfer device; and
   attaching the first and second discrete segments to each other at the application location to form a web.

2. The method as set forth in claim 1 wherein transferring the first discrete segment comprises accelerating the first discrete segment from a first transfer speed at the first pick-up location to a second, faster transfer speed at the application location, and wherein transferring the second discrete segment comprises accelerating the second discrete segment from a first transfer speed at the pick-up location to a second, faster transfer speed at the application location.

3. The method as set forth in claim 2 wherein the second transfer speed of the first discrete segment at the application location is approximately equal to the second transfer speed of the second discrete segment at the application location.

4. The method as set forth in claim 2 wherein the first transfer speed of the first discrete segment at the first pick-up location is different than the first transfer speed of the second discrete segment at the second pick-up location.

5. The method as set forth in claim 1 wherein directing the first discrete segment to the first pick-up location comprises feeding a continuous web at the first speed to the first pick-up location.

6. The method as set forth in claim 5 wherein directing the second discrete segment to the second pick-up location comprise feeding a continuous web at the second speed to the second pick-up location.

7. The method as set forth in claim 1 wherein attaching the first and second discrete segments to each other at the application location comprises engaging a hook fastener member on the first discrete segment with a complementary, loop fastener member on the second discrete segment such that the first and second discrete segments are releasably engaged by the hook and loop fastener members.

8. The method as set forth in claim 1 wherein the first and second segment transfer devices comprise oscillating cam adjusted rollers.

9. A method of joining discrete segments comprising:
   directing a plurality of first discrete segments having a first length to a first pick-up location;
   transferring the plurality of first discrete segments from the first pick-up location to an application location using a first segment transfer device, the first segment transfer device being sized and shaped to receive at least two of the plurality of the first discrete segments,
   directing a plurality of second discrete segments at a second speed to a second pick-up location;
   transferring the plurality of second discrete segment from the second pick-up location to the application location using a second segment transfer device; and
   attaching the plurality of first discrete segments to the plurality of discrete second segments by aligning each other at the application location to form a continuous web of alternating first and second discrete segments.

10. The method as set forth in claim 9 wherein transferring the plurality of first discrete segments comprises accelerating the plurality of first discrete segments from a first transfer speed at the first pick-up location to a second, faster transfer speed at the application location, and wherein transferring the plurality of second discrete segments comprises accelerating the plurality of second discrete segments from a first transfer speed at the pick-up location to a second, faster transfer speed at the application location.

11. The method as set forth in claim 10 wherein the second transfer speed of the plurality of first discrete segments at the application location is approximately equal to the second transfer speed of the plurality of second discrete segments at the application location.

12. The method as set forth in claim 10 wherein the first transfer speed of the plurality of first discrete segments at the first pick-up location is different than the first transfer speed of the plurality of second discrete segments at the second pick-up location.

13. The method as set forth in claim 9 wherein directing the plurality of first discrete segments to the first pick-up location comprises feeding a continuous web at a first speed to the first pick-up location.

14. The method as set forth in claim 13 wherein directing the plurality of second discrete segments to the second pick-up location comprise feeding a continuous web at the second speed to the second pick-up location.

15. The method as set forth in claim 9 wherein attaching each of the plurality of first and second discrete segments to each other at the application location comprises engaging a hook fastener member on each of the plurality of first discrete segments with a complementary, loop fastener member on each of the plurality of second discrete segments.

16. The method as set forth in claim 9 wherein the first and second segment transfer devices comprise oscillating cam adjusted rollers.

17. A method of joining discrete segments comprising:
   rotating a first discrete segment coupled to and extending outward from a first segment transfer device comprising a plurality of transfer elements, each transfer element having a first leading edge and a first trailing edge, the first segment transfer device being adapted to rotate each transfer element about a drive axis at a first variable speed profile;
   transferring the first discrete segment from a first pick-up location to an application location;
   rotating a second discrete segment coupled to and extending outward from a second segment transfer device comprising a plurality of transfer elements, each transfer element having a first leading edge and a first trailing edge, the second segment transfer device being adapted to rotate each transfer element about the drive axis at a second variable speed profile;

transferring the second discrete segment from a second pick-up location to the application location; and attaching the first and second discrete segments to each other at the application location to form a web wherein the continuous web is defined by a plurality of alternating first and second discrete segments.

18. The method as set forth in claim 17 further comprising bonding a pair of spaced-apart first fastener members to the first discrete segment, and bonding a pair of spaced-apart second fastener members to the second discrete segment, wherein the resulting web is defined by the first and second discrete segments being secured to each other by the first and second fastener members.

19. The method as set forth in claim 18, wherein each of the transfer elements of the first segment transfer device has a first speed profile, and each of the transfer elements of the second segment transfer device has a second speed profile that is different than the first speed profile.

20. The method as set forth in claim 17 wherein each of the transfer elements of the first segment transfer device has a first speed profile, and each of the transfer elements of the second segment transfer device has a second speed profile that is the same as the first speed profile.

* * * * *